US012303316B2

(12) United States Patent
Liu et al.

(10) Patent No.: US 12,303,316 B2
(45) Date of Patent: May 20, 2025

(54) IMAGING METHOD COMPRISING MOVING AN IMAGE SENSOR ALONG A FIRST DIRECTION AMONG A PLURALITY OF POSITIONS RELATIVE TO A SCENE AND CAPTURING PARTIAL IMAGE OF THE SCENE RESPECTIVELY AT THE PLURALITY OF POSITIONS

(71) Applicant: SHENZHEN XPECTVISION TECHNOLOGY CO., LTD., Shenzhen (CN)

(72) Inventors: Yurun Liu, Shenzhen (CN); Peiyan Cao, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 201 days.

(21) Appl. No.: 18/196,004

(22) Filed: May 11, 2023

(65) Prior Publication Data

US 2023/0280485 A1    Sep. 7, 2023

Related U.S. Application Data

(63) Continuation of application No. PCT/CN2020/131471, filed on Nov. 25, 2020.

(51) Int. Cl.
*A61B 6/00* (2024.01)
*A61B 6/40* (2024.01)
(Continued)

(52) U.S. Cl.
CPC .......... *A61B 6/5241* (2013.01); *A61B 6/4233* (2013.01); *A61B 6/4266* (2013.01);
(Continued)

(58) Field of Classification Search
CPC ... A61B 6/4078; A61B 6/4085; A61B 6/4233; A61B 6/4241; A61B 6/4266;
(Continued)

(56) References Cited

U.S. PATENT DOCUMENTS 6,097,833 A * 8/2000 Lobregt ................. A61B 6/481
378/98.12
6,463,121 B1 * 10/2002 Milnes ................. A61B 6/4482
378/98.2
(Continued)

FOREIGN PATENT DOCUMENTS

CN    102599926 A    7/2012
CN    108271415 A    7/2018
(Continued)

*Primary Examiner* — Allen C. Ho
(74) *Attorney, Agent, or Firm* — IPro, PLLC (57) ABSTRACT

Disclosed herein is a method comprising: moving an image sensor along a first direction among a plurality of positions relative to a scene and capturing partial images of the scene respectively at the plurality of positions; forming an image of the scene from the partial images; wherein the image sensor has an active area and a dead zone; wherein the dead zone extends along a second direction; wherein the second direction is at an angle with the first direction; wherein each point in the scene falls on the dead zone no more than once when the image sensor is at the plurality of positions.

19 Claims, 10 Drawing Sheets

(51) Int. Cl.
*A61B 6/42* (2024.01)
*A61B 6/50* (2024.01)
*G01N 23/04* (2018.01)
*G01T 1/24* (2006.01)
*G01T 1/29* (2006.01)
*G01T 1/36* (2006.01)
*G01T 1/38* (2006.01)

(52) U.S. Cl.
CPC ........... *A61B 6/4452* (2013.01); *G01N 23/04* (2013.01); *G01T 1/243* (2013.01); *G01T 1/2928* (2013.01); *G01T 1/2978* (2013.01); *G01T 1/366* (2013.01); *G01T 1/38* (2013.01)

(58) Field of Classification Search
CPC ... A61B 6/4283; A61B 6/4429; A61B 6/4435; A61B 6/4441; A61B 6/4447; A61B 6/4452; A61B 6/5241; G01N 23/04; G01N 23/043; G01N 23/10; G01N 23/18; G01T 1/24; G01T 1/243; G01T 1/29; G01T 1/2914; G01T 1/2921; G01T 1/2928; G01T 1/2964; G01T 1/2971
USPC ............. 378/62, 98.8, 98.12, 146, 189, 190; 250/370.09
See application file for complete search history.

(56) References Cited

U.S. PATENT DOCUMENTS

| | | | | |
|---|---|---|---|---|
| 6,587,598 B1* | 7/2003 | Devillers | ................ | G06T 7/223 |
| | | | | 382/284 |
| 6,898,269 B2* | 5/2005 | Halsmer | .............. | A61B 6/4233 |
| | | | | 378/146 |
| 7,123,779 B2* | 10/2006 | Beuker | ................ | A61B 6/5241 |
| | | | | 382/284 |
| 7,142,632 B2* | 11/2006 | Atzinger | .............. | A61B 6/4464 |
| | | | | 378/62 |
| 7,212,605 B2* | 5/2007 | Danielsson | ........... | G01T 1/1644 |
| | | | | 378/146 |
| 7,522,701 B2* | 4/2009 | Jensen | ...................... | G06T 5/50 |
| | | | | 378/98.12 |
| 7,555,100 B2* | 6/2009 | Wang | ................... | H04N 5/2624 |
| | | | | 378/98.12 |
| 7,881,434 B2* | 2/2011 | Akahori | ............... | A61B 6/5229 |
| | | | | 378/98.12 |
| 8,064,572 B2* | 11/2011 | Sato | ..................... | A61B 6/5241 |
| | | | | 378/62 |
| 8,084,744 B2* | 12/2011 | Enomoto | ............. | H04N 23/698 |
| | | | | 378/62 |
| 8,344,327 B2* | 1/2013 | Yamaguchi | ............ | A61B 6/582 |
| | | | | 250/363.07 |
| 8,360,639 B2* | 1/2013 | Kato | ....................... | A61B 6/587 |
| | | | | 378/197 |
| 8,385,623 B2* | 2/2013 | Sakai | .................... | A61B 6/589 |
| | | | | 378/62 |
| 8,550,709 B2* | 10/2013 | Nishino | ................... | A61B 6/06 |
| | | | | 378/207 |
| 8,767,913 B2* | 7/2014 | Okuno | ................... | G01N 23/04 |
| | | | | 378/62 |
| 8,792,616 B2* | 7/2014 | Tanaka | ................... | A61B 6/527 |
| | | | | 378/205 |
| 8,873,709 B2* | 10/2014 | Kimura | .................. | A61B 6/505 |
| | | | | 378/197 |
| 8,908,832 B2* | 12/2014 | Yamashita | ............... | A61B 6/06 |
| | | | | 378/98.12 |
| 9,109,998 B2* | 8/2015 | Nathaniel | ............. | G01N 23/04 |
| 9,541,509 B2* | 1/2017 | Akahori | ................ | A61B 6/527 |
| 9,814,435 B2* | 11/2017 | Kim | ...................... | A61B 6/5241 |
| 9,820,703 B2* | 11/2017 | Wojcik | ................. | A61B 6/4233 |
| 10,007,009 B2* | 6/2018 | Cao | ......................... | G01T 1/247 |
| 10,034,643 B2* | 7/2018 | Kim | ......................... | A61B 6/544 |
| 10,061,038 B2* | 8/2018 | Cao | ............................ | G01T 7/00 |
| 10,380,718 B2* | 8/2019 | Moon | ........................ | G06T 3/20 |
| 10,546,398 B2* | 1/2020 | Kaltschmidt | ........ | A61B 6/5241 |
| 10,660,581 B2* | 5/2020 | Fieselmann | .......... | A61B 6/4452 |
| 10,702,229 B2* | 7/2020 | Lee | ......................... | A61B 6/467 |
| 10,945,688 B2* | 3/2021 | Cao | ......................... | A61B 6/4241 |
| 10,989,820 B2* | 4/2021 | Cao | .......................... | G01V 5/222 |
| 11,032,500 B2* | 6/2021 | Cao | ........................ | G06T 7/0012 |
| 11,051,778 B2* | 7/2021 | Tanaka | ................. | A61B 6/0487 |
| 11,114,425 B2* | 9/2021 | Cao | .......................... | H01R 12/52 |
| 11,199,633 B2* | 12/2021 | Cao | ........................ | H10F 30/301 |
| 11,224,388 B2* | 1/2022 | Cao | .......................... | G01T 1/249 |
| 11,291,420 B2* | 4/2022 | Cao | ........................ | A61B 6/4411 |
| 11,454,731 B2* | 9/2022 | Cao | ............................ | G01T 1/16 |
| 11,612,373 B2* | 3/2023 | Park | ..................... | A61B 6/0407 |
| | | | | 378/62 |
| 11,668,660 B2* | 6/2023 | Nisius | ................... | G01N 23/04 |
| | | | | 378/60 |
| 11,806,178 B2* | 11/2023 | Kitano | ................... | A61B 6/589 |
| 11,821,850 B2* | 11/2023 | Venkatachalam | ...... | G01N 23/06 |
| 11,825,201 B2* | 11/2023 | Cao | ........................ | H04N 23/695 |
| 11,826,188 B2* | 11/2023 | Wear | ..................... | A61B 6/486 |
| 11,852,760 B2* | 12/2023 | Cao | ........................... | G01T 1/24 |
| 11,941,850 B2* | 3/2024 | Liu | ............................ | G06T 3/02 |
| 11,948,285 B2* | 4/2024 | Cao | ........................... | A61B 6/40 |
| 12,011,308 B2* | 6/2024 | Cao | ........................ | G06T 7/0012 |
| 12,019,193 B2* | 6/2024 | Liu | ...................... | A61B 6/4233 |
| 12,133,750 B2* | 11/2024 | Takezawa | ............. | A61B 6/481 |
| 2002/0018543 A1 | 2/2002 | Danielsson | | |
| 2004/0012689 A1 | 1/2004 | Tinnerino et al. | | |
| 2019/0069858 A1 | 3/2019 | Cao et al. | | |

FOREIGN PATENT DOCUMENTS

| | | |
|---|---|---|
| CN | 109690351 A | 4/2019 |
| TW | 201824855 A | 7/2018 |
| WO | 2008003351 A1 | 1/2008 |
| WO | 2012029974 A1 | 3/2012 |
| WO | 2020056613 A1 | 3/2020 |
| WO | 2020056712 A1 | 3/2020 |

\* cited by examiner

IMAGING METHOD COMPRISING MOVING AN IMAGE SENSOR ALONG A FIRST DIRECTION AMONG A PLURALITY OF POSITIONS RELATIVE TO A SCENE AND CAPTURING PARTIAL IMAGE OF THE SCENE RESPECTIVELY AT THE PLURALITY OF POSITIONS

BACKGROUND

Radiation detectors may be devices used to measure the flux, spatial distribution, spectrum or other properties of radiations.

Radiation detectors may be used for many applications. One important application is imaging. Radiation imaging is a radiography technique and can be used to reveal the internal structure of a non-uniformly composed and opaque object such as the human body.

Early radiation detectors for imaging include photographic plates and photographic films. A photographic plate may be a glass plate with a coating of light-sensitive emulsion. Although photographic plates were replaced by photographic films, they may still be used in special situations due to the superior quality they offer and their extreme stability. A photographic film may be a plastic film (e.g., a strip or sheet) with a coating of light-sensitive emulsion.

In the 1980s, photostimulable phosphor plates (PSP plates) became available. A PSP plate may contain a phosphor material with color centers in its lattice. When the PSP plate is exposed to radiation, electrons excited by radiation are trapped in the color centers until they are stimulated by a laser beam scanning over the plate surface. As the plate is scanned by laser, trapped excited electrons give off light, which is collected by a photomultiplier tube. The collected light is converted into a digital image. In contrast to photographic plates and photographic films, PSP plates can be reused.

Another kind of radiation detectors are radiation image intensifiers. Components of a radiation image intensifier are usually sealed in a vacuum. In contrast to photographic plates, photographic films, and PSP plates, Radiation image intensifiers may produce real-time images, i.e., do not require post-exposure processing to produce images. Radiation first hits an input phosphor (e.g., cesium iodide) and is converted to visible light. The visible light then hits a photocathode (e.g., a thin metal layer containing cesium and antimony compounds) and causes emission of electrons. The number of emitted electrons is proportional to the intensity of the incident Radiation. The emitted electrons are projected, through electron optics, onto an output phosphor and cause the output phosphor to produce a visible-light image.

Scintillators operate somewhat similarly to radiation image intensifiers in that scintillators (e.g., sodium iodide) absorb radiation and emit visible light, which can then be detected by a suitable image sensor for visible light. In scintillators, the visible light spreads and scatters in all directions and thus reduces spatial resolution. Reducing the scintillator thickness helps to improve the spatial resolution but also reduces absorption of radiation. A scintillator thus has to strike a compromise between absorption efficiency and resolution.

Semiconductor radiation detectors largely overcome this problem by direct conversion of radiation into electric signals. A semiconductor radiation detector may include a semiconductor layer that absorbs radiation in wavelengths of interest. When a particle of radiation is absorbed in the semiconductor layer, multiple charge carriers (e.g., electrons and holes) are generated and swept under an electric field towards electric contacts on the semiconductor layer. Cumbersome heat management required in currently available semiconductor radiation detectors (e.g., Medipix) can make a detector with a large area and a large number of pixels difficult or impossible to produce.

SUMMARY

Disclosed herein is a method comprising: moving an image sensor along a first direction among a plurality of positions relative to a scene and capturing partial images of the scene respectively at the plurality of positions; forming an image of the scene from the partial images; wherein the image sensor has an active area and a dead zone; wherein the dead zone extends along a second direction; wherein the second direction is at an angle with the first direction; wherein each point in the scene falls on the dead zone no more than once when the image sensor is at the plurality of positions.

According to an embodiment, the dead zone extends across the active area.

According to an embodiment, the dead zone divides the active area into multiple spatially discontinuous portions.

According to an embodiment, the image sensor comprises a plurality of radiation detectors.

According to an embodiment, the dead zone is part of a guard ring of the radiation detectors.

According to an embodiment, the plurality of radiation detectors overlap one another.

According to an embodiment, at least one of the plurality of radiation detectors has an edge parallel to the first direction.

According to an embodiment, the method further comprises forming projections of guard rings in the first image and the second image.

According to an embodiment, the image sensor comprises a plurality of pixels; wherein the image sensor is configured to count numbers of particles of radiation incident on the pixels, within a period of time.

According to an embodiment, the particles of radiation are X-ray photons.

According to an embodiment, at least one of the radiation detectors comprises a radiation absorption layer comprising an electric contact; a first voltage comparator configured to compare a voltage of the electric contact to a first threshold; a second voltage comparator configured to compare the voltage to a second threshold; a counter configured to register a number of radiation photons or particles reaching the radiation absorption layer; a controller; wherein the controller is configured to start a time delay from a time at which the first voltage comparator determines that an absolute value of the voltage equals or exceeds an absolute value of the first threshold; wherein the controller is configured to activate the second voltage comparator during the time delay; wherein the controller is configured to cause the number registered by the counter to increase by one, when the second voltage comparator determines that an absolute value of the voltage equals or exceeds an absolute value of the second threshold.

According to an embodiment, the image sensor further comprises an integrator electrically connected to the electric contact, wherein the integrator is configured to collect charge carriers from the electric contact.

According to an embodiment, the controller is configured to activate the second voltage comparator at a beginning or expiration of the time delay.

According to an embodiment, the controller is configured to connect the electric contact to an electrical ground.

According to an embodiment, a rate of change of the voltage is substantially zero at expiration of the time delay.

According to an embodiment, the radiation absorption layer comprises a diode.

According to an embodiment, the radiation absorption layer comprises single-crystalline silicon.

According to an embodiment, the image sensor does not comprise a scintillator.

DETAILED DESCRIPTION

Figure 1:
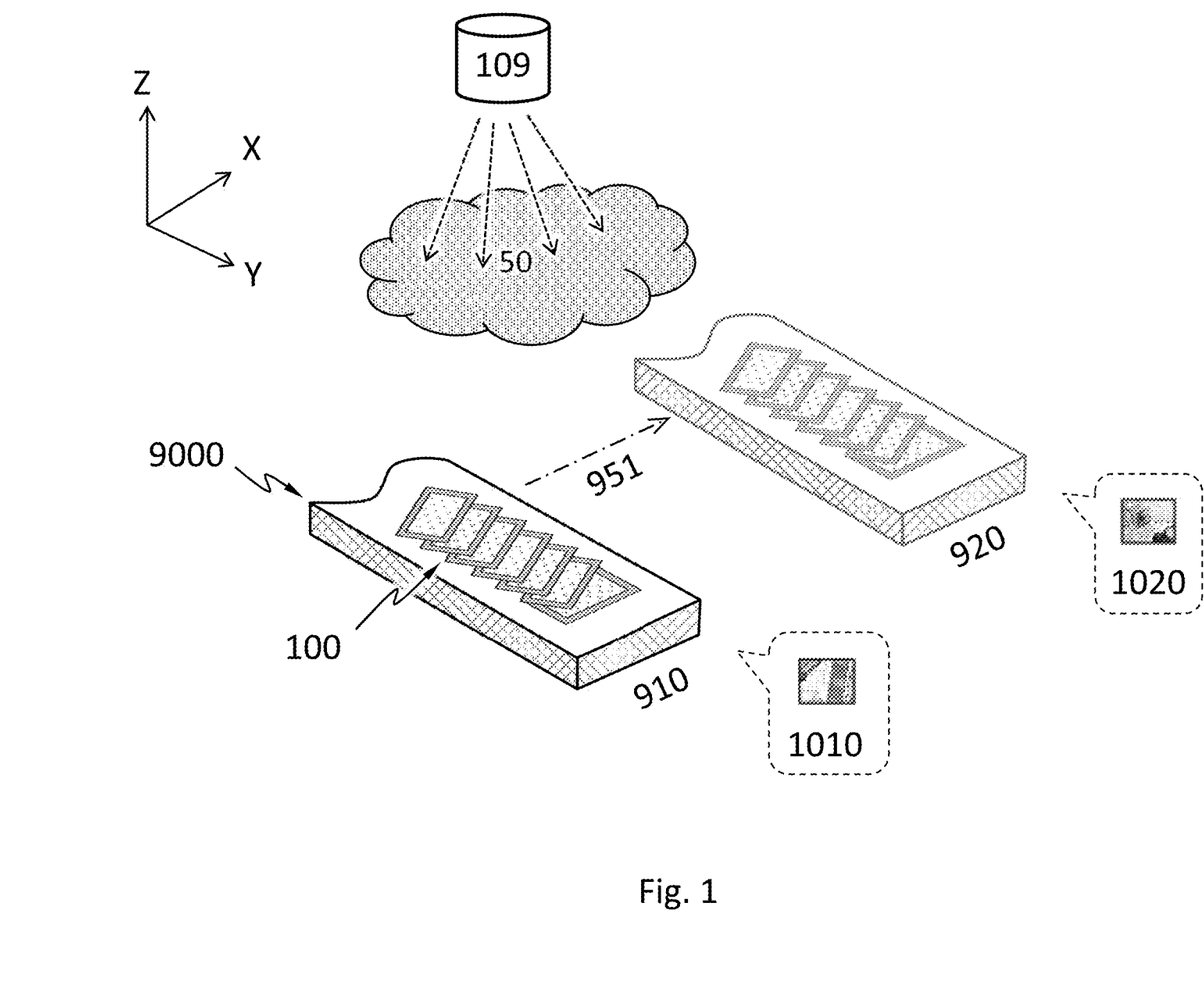
FIG. 1 schematically show a method of moving an image sensor along a first direction among a plurality of positions relative to a scene and capturing partial images of the scene respectively at the plurality of positions, according to an embodiment.

FIG. 1 schematically shows a method, according to an embodiment. The method includes moving an image sensor 9000 along a first direction 951 among a plurality of positions relative to a scene 50 and capturing partial images of the scene 50 respectively at the plurality of positions.

In the example shown in FIG. 1, the image sensor 9000 may move from the first position 910 relative to the scene 50 to a second position 920 along the first direction 951. In one embodiment, at the first position 910 relative to the scene 50, the image sensor 9000 captures a partial image 1010 of portions of the scene 50 using a radiation from a radiation source 109 that has passed through the scene 50; and at the second position 920 relative to the scene 50, the image sensor 9000 captures another partial image 1020 of portions of the scene 50 using the radiation from the radiation source 109 that has passed through the scene 50. The image sensor 9000 may comprise a plurality of radiation detectors 100 configured to receive the radiation incident thereon from the radiation source 109.

Figures 2A, 2B:
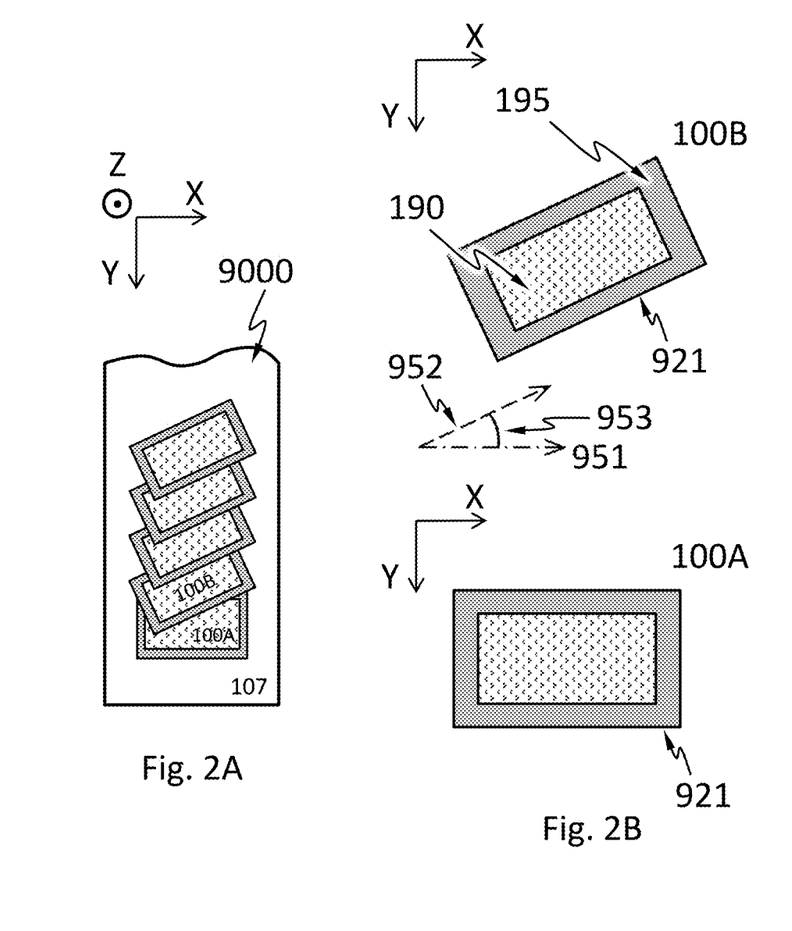
FIG. 2A schematically shows the image sensor comprising a plurality of radiation detectors, according an embodiment.
FIG. 2B schematically shows top views of a first radiation detector and a second radiation detector, according to an embodiment.
Figure 2C:
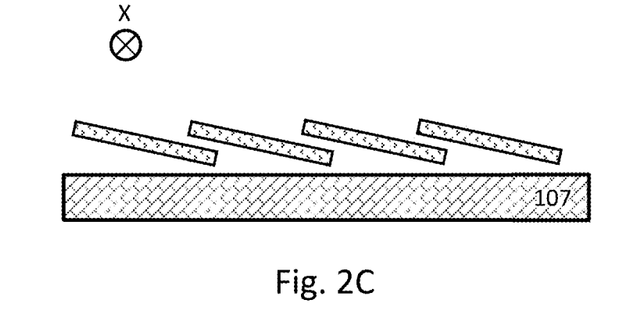
FIG. 2C-2D each schematically shows side views of two different arrangements of the radiation detectors of the image sensor, according to an embodiment.
Figure 2D:
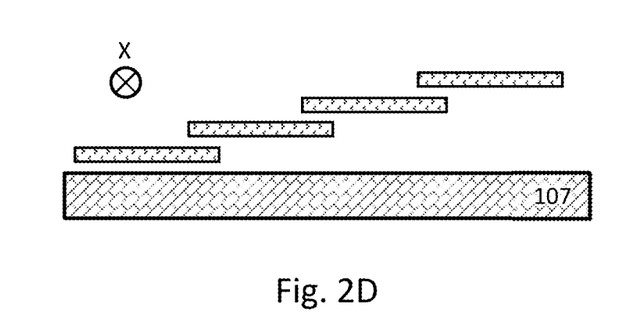

FIGS. 2A-2D schematically show that the image sensor 9000 may comprise a plurality of radiation detectors 100 (e.g., a first radiation detector 100A, a second radiation detector 100B) according to an embodiment. The image sensor 9000 may comprise a support 107 such as a print circuit board (PCB). FIG. 2A schematically shows a top view of a portion of the image sensor 9000, according to one embodiment. The plurality of radiation detectors 100 may be arranged on a planar surface of the support 107 thereon. FIGS. 2C-2D schematically shows side views of two different arrangements of the radiation detectors 100 of the image sensor 9000, according to one embodiment. In the example shown in FIG. 2C, the plurality of radiation detectors 100 may be mounted on the support 107, and each radiation detector's radiation-receiving surface may be tilted relative to the planar surface of the support 107. The plurality of radiation detectors 100 may be overlap one another. In the example shown in FIG. 2D, the plurality of radiation detectors 100 may be mounted on the support 107, and each radiation detector's radiation-receiving surface may be parallel relative to the planar surface of the support 107.

FIG. 2B schematically shows top views of the first radiation detector 100A and the second radiation detector 100B, according to an embodiment. The first radiation detector 100A may be arranged in different orientation than the second radiation detector 100B. In the example shown in FIG. 2B, the first radiation detector 100A may have an edge 921 parallel to the first direction 951. In one embodiment, the image sensor 9000 includes at least one first radiation detector 100A. The second radiation detector 100B may be tilted relative to the first direction 951 such that one edge 921 of the second radiation detector 100B may be parallel to a second direction 952. The second direction 952 is not parallel to the first direction 951, according to one embodiment. The second direction 952 may be at an angle 953 (e.g., larger than 10 degrees, 20 degrees, or 30 degrees, etc.) relative to the first direction 951. As used herein, "at an angle" means not parallel or perpendicular.

The radiation detectors 100 (as shown in FIG. 2B) have an active area 190, and a dead zone 195 respectively, according to an embodiment. The active area 190 may comprise plurality of pixels 150 so that when the radiation detectors 100 receive radiation from the radiation source 109 that has passed through the scene 50, the pixels 150 may detect incident particles of the radiation. The dead zone 195 may be a perimeter area surrounding the radiation-receiving surface of the radiation detectors 100 that comprises no pixels, therefore particles of radiation incident in the dead zone 195 may not be detected by the radiation detectors 100. In one embodiment, the dead zone 195 is also a part of a guard ring of the radiation detectors 100. The dead zone 195 may extend across the active area 190 respectively in each radiation detector. In one embodiment, when multiple radiation detectors 100 (e.g., 100A, 100B, etc.) arranged together to form the image sensor 9000 as shown in FIG. 2A, the active area of the image sensor 9000 is divided into multiple spatially discontinuous portions by the dead zones 195. The dead zone of the image sensor 9000 may include the dead zones of the radiation detectors 100 and any gaps among the radiation detectors 100. The active area of the image sensor 9000 is the combination of the active areas 190 of the radiation detectors 100.

Figure 3:
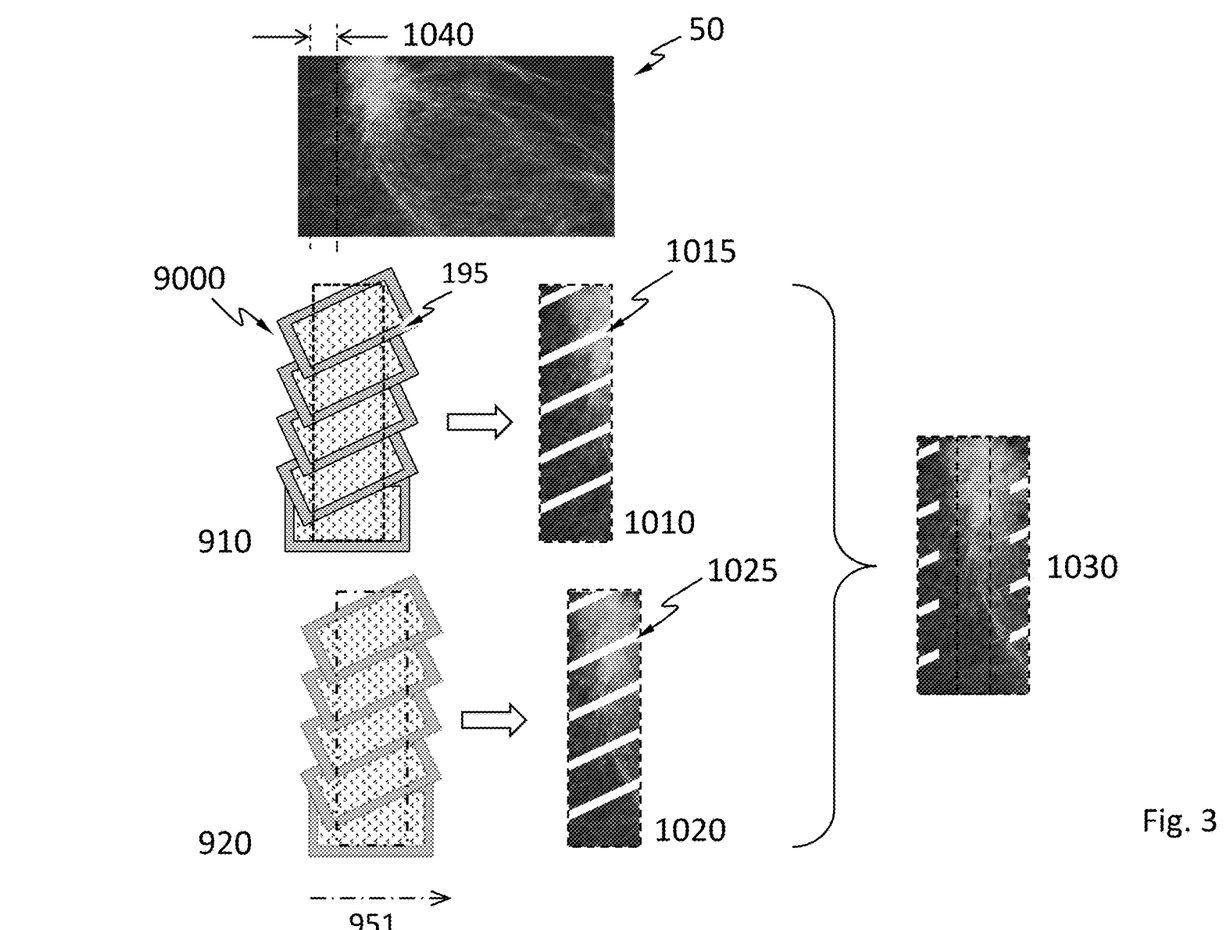
FIG. 3 schematically shows the image sensor capturing a plurality of partial images of portions of the scene, according to an embodiment.

FIG. 3 schematically shows the image sensor 9000 capturing a plurality of images of portions of the scene 50, according to an embodiment. In the example shown in FIG. 3, the image sensor 9000 comprising multiple radiation detectors 100 may move from the position 910 along the first direction 951 relative to the scene 50 to the position 920. The image sensor 9000 may capture partial images 1010 and 1020 of the portions of the scene 50 at the position 910 and the position 920, respectively. The image sensor 9000 may stitch the partial images 1010 and 1020 to form an image 1030 of the entire scene 50. The dead zone of the image sensor 9000 leave voids in the partial images 1010 and 1020. In the example shown in FIG. 3, void 1015 in the partial image 1010 is left by the dead zone when the image sensor 9000 is at the position 910; void 1025 in the partial image 1020 is left by the dead zone when the image sensor 9000 is at the position 920, according to one embodiment. In one embodiment, the image sensor 9000 moves from position 910 to the position 920 following a minimum step size 1040 so that each point in the scene 50 falls on the dead zone of the image sensor 9000 no more than once when the image sensor 9000 is at the plurality of positions. Therefore, a point of the scene 50 falling on the dead zone of the image sensor 9000 at the position 910 may be captured by the image sensor 9000 when the image sensor 9000 is at the position 920. By maintaining the minimum step size 1040 for every move of the image sensor 9000 along the first direction 951, the image 1030 of entire scene 50 can be formed by combining the partial images (i.e., 1010, 1020, etc.) captured by the image sensor 9000 at the plurality of positions.

Figure 4:
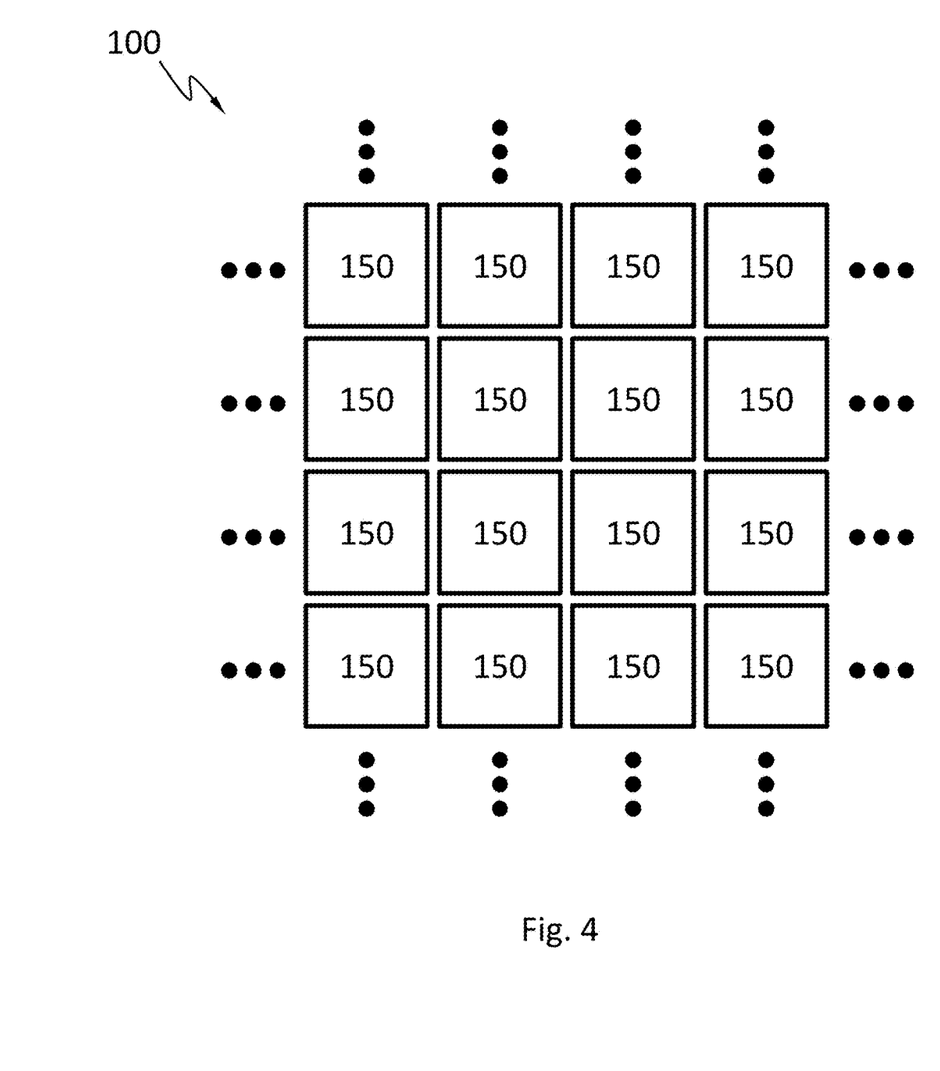
FIG. 4 schematically shows that the radiation detector may have an array of pixels, according to an embodiment.

FIG. 4 schematically shows that the radiation detector 100 may have an array of pixels 150, according to an embodiment. The array may be a rectangular array, a honeycomb array, a hexagonal array or any other suitable array. Each pixel 150 may be configured to detect a particle of radiation incident thereon, measure the energy of the particle of radiation, or both. For example, each pixel 150 may be configured to count numbers of particles of radiation incident thereon whose energy falls in a plurality of bins, within a period of time. All the pixels 150 may be configured to count the numbers of particles of radiation incident thereon within a plurality of bins of energy within the same period of time. Each pixel 150 may have its own analog-to-digital converter (ADC) configured to digitize an analog signal representing the energy of an incident particle of radiation into a digital signal. The ADC may have a resolution of 10 bits or higher. Each pixel 150 may be configured to measure its dark current, such as before or concurrently with each particle of radiation incident thereon. Each pixel 150 may be configured to deduct the contribution of the dark current from the energy of the particle of radiation incident thereon. The pixels 150 may be configured to operate in parallel. For example, when one pixel 150 measures an incident particle of radiation, another pixel 150 may be waiting for another particle of radiation to arrive. The pixels 150 may be but do not have to be individually addressable. The particles of radiation may be X-ray photons.

Figure 5A:
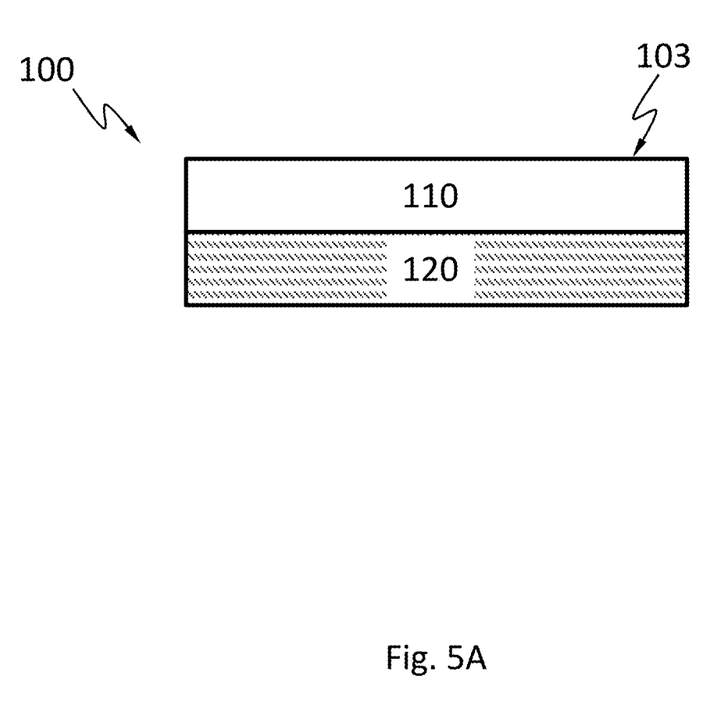
FIG. 5A schematically shows a cross-sectional view of the radiation detector, according to an embodiment.

FIG. 5A schematically shows a cross-sectional view of one of the radiation detectors 100, according to an embodiment. The radiation detector 100 may include a radiation absorption layer 110 and an electronics layer 120 (e.g., an ASIC) for processing or analyzing electrical signals incident radiation generates in the radiation absorption layer 110. In one embodiment, the radiation detector 100 of the image sensor 9000 does not comprise a scintillator. The radiation absorption layer 110 may comprise a semiconductor material such as, silicon, germanium, GaAs, CdTe, CdZnTe, or single-crystalline silicon. The semiconductor may have a high mass attenuation coefficient for the radiation energy of interest. The surface 103 of the radiation absorption layer 110 distal from the electronics layer 120 is configured to receive radiation.

Figure 5B:
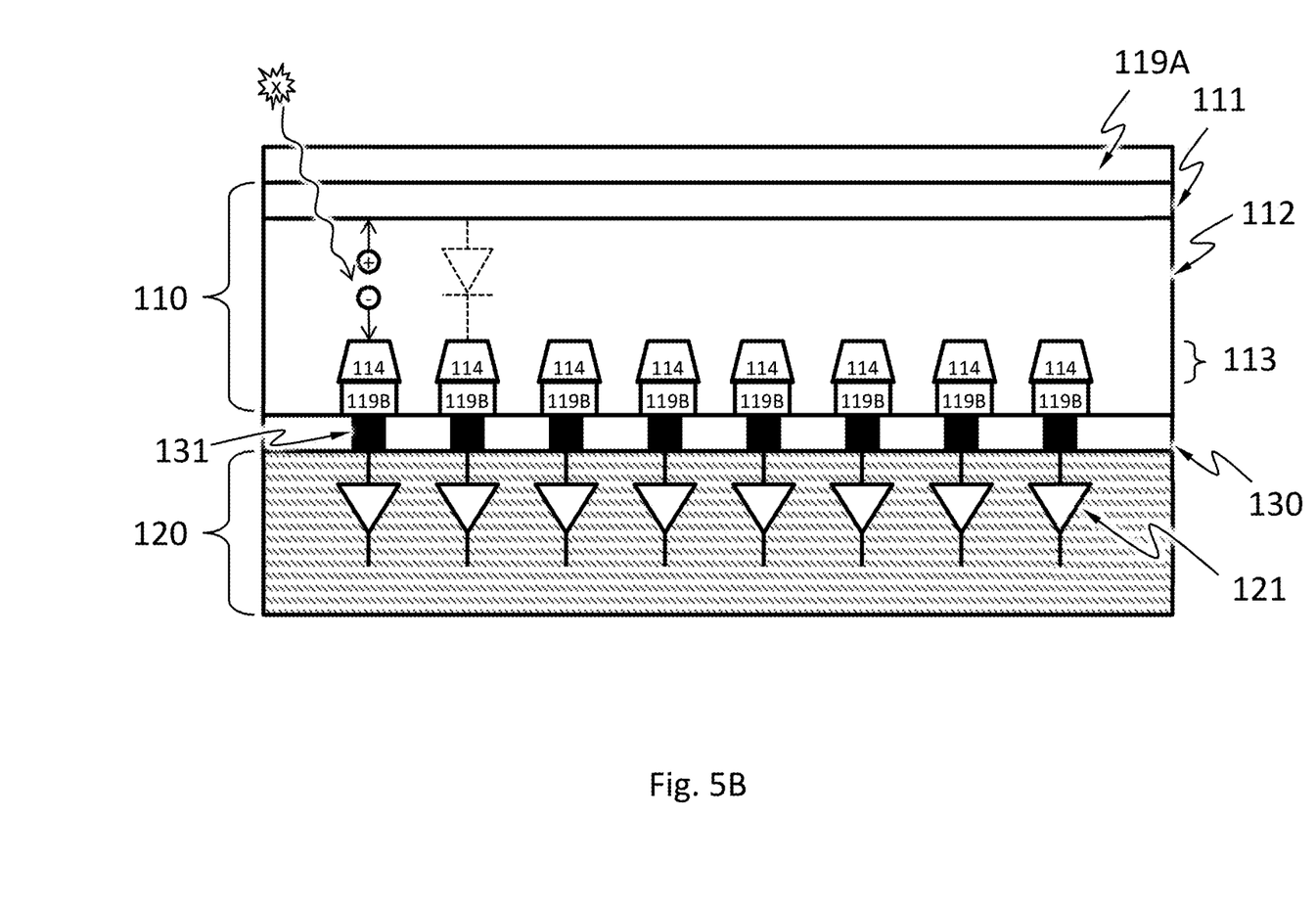
FIG. 5B schematically shows a detailed cross-sectional view of the radiation detector, according to an embodiment.

As shown in a detailed cross-sectional view of the radiation detector 100 in FIG. 5B, according to an embodiment, the radiation absorption layer 110 may include one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete regions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 5B, each of the discrete regions 114 of the second doped region 113 forms a diode with the first doped region 111 and the optional intrinsic region 112. Namely, in the example in FIG. 5B, the radiation absorption layer 110 has a plurality of diodes having the first doped region 111 as a shared electric contact. The first doped region 111 may also have discrete portions.

When a particle of radiation hits the radiation absorption layer 110 including diodes, the particle of radiation may be absorbed and generate one or more charge carriers by a number of mechanisms. A particle of radiation may generate 10 to 100000 charge carriers. The charge carriers may drift to the electric contacts of one of the diodes under an electric field. The field may be an external electric field. The electric contact 119B may include discrete portions each of which is in electrical contact with the discrete regions 114. In an embodiment, the charge carriers may drift in directions such that the charge carriers generated by a single particle of radiation are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by a particle of radiation incident around the footprint of one of these discrete regions 114 are not substantially shared with another of these discrete regions 114. The pixel 150 associated with a discrete region 114 may be an area around the discrete region 114 in which substantially all (more than 98%, more than 99.5%, more than 99.9%, or more than 99.99% of) charge carriers generated by a particle of radiation incident therein at an angle of incidence of 0° flow to the discrete region 114. Namely, less than 2%, less than 1%, less than 0.1%, or less than 0.01% of these charge carriers flow beyond the pixel.

Figure 5C:
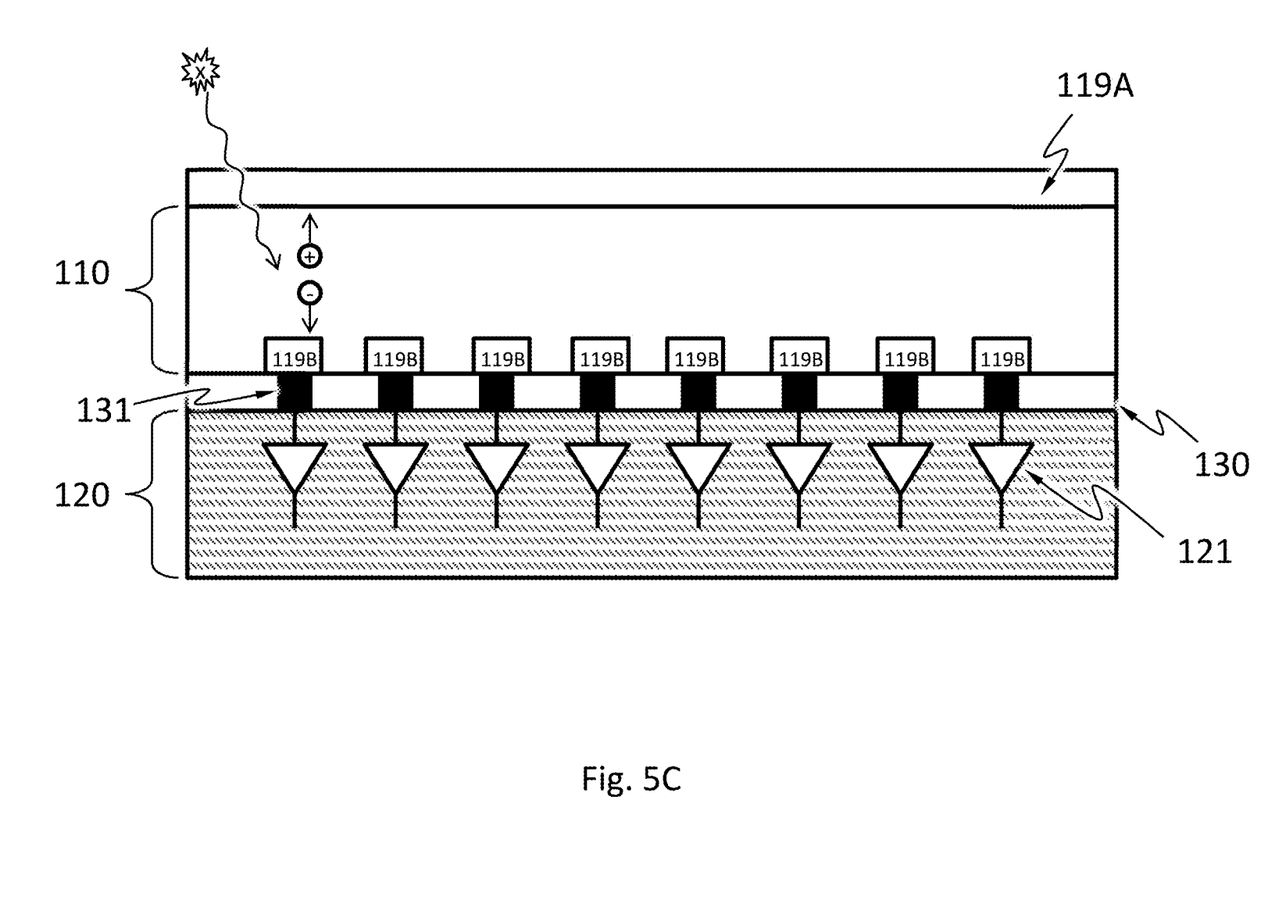
FIG. 5C schematically shows an alternative detailed cross-sectional view of the radiation detector, according to an embodiment.

As shown in an alternative detailed cross-sectional view of the radiation detector 100 in FIG. 5C, according to an embodiment, the radiation absorption layer 110 may comprise a resistor of a semiconductor material such as, silicon, germanium, GaAs, CdTe, CdZnTe, or a combination thereof, but does not include a diode. The semiconductor may have a high mass attenuation coefficient for the radiation energy of interest.

When a particle of radiation hits the radiation absorption layer 110 comprising a resistor but not diodes, it may be absorbed and generate one or more charge carriers by a number of mechanisms. A particle of radiation may generate 10 to 100000 charge carriers. The charge carriers may drift to the electric contacts 119A and 119B under an electric field. The field may be an external electric field. The electric contact 119B includes discrete portions. In an embodiment, the charge carriers may drift in directions such that the charge carriers generated by a single particle of radiation are not substantially shared by two different discrete portions of the electric contact 119B ("not substantially shared" here means less than 2%, less than 0.5%, less than 0.1%, or less than 0.01% of these charge carriers flow to a different one of the discrete portions than the rest of the charge carriers). Charge carriers generated by a particle of radiation incident around the footprint of one of these discrete portions of the electric contact 119B are not substantially shared with another of these discrete portions of the electric contact 119B. The pixel 150 associated with a discrete portion of the electric contact 119B may be an area around the discrete portion in which substantially all (more than 98%, more than 99.5%, more than 99.9% or more than 99.99% of) charge carriers generated by a particle of radiation incident at an angle of incidence of 0° therein flow to the discrete portion of the electric contact 119B. Namely, less than 2%, less than 0.5%, less than 0.1%, or less than 0.01% of these charge carriers flow beyond the pixel associated with the one discrete portion of the electric contact 119B.

The electronics layer 120 may include an electronic system 121 suitable for processing or interpreting signals generated by particles of radiation incident on the Radiation absorption layer 110. The electronic system 121 may include an analog circuitry such as a filter network, amplifiers, integrators, and comparators, or a digital circuitry such as a microprocessor, and memory. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the pixels by vias 131. Space among the vias may be filled with a filler material 130, which may increase the mechanical stability of the connection of the electronics layer 120 to the radiation absorption layer 110. Other bonding techniques are possible to connect the electronic system 121 to the pixels without using vias.

Figure 6A:
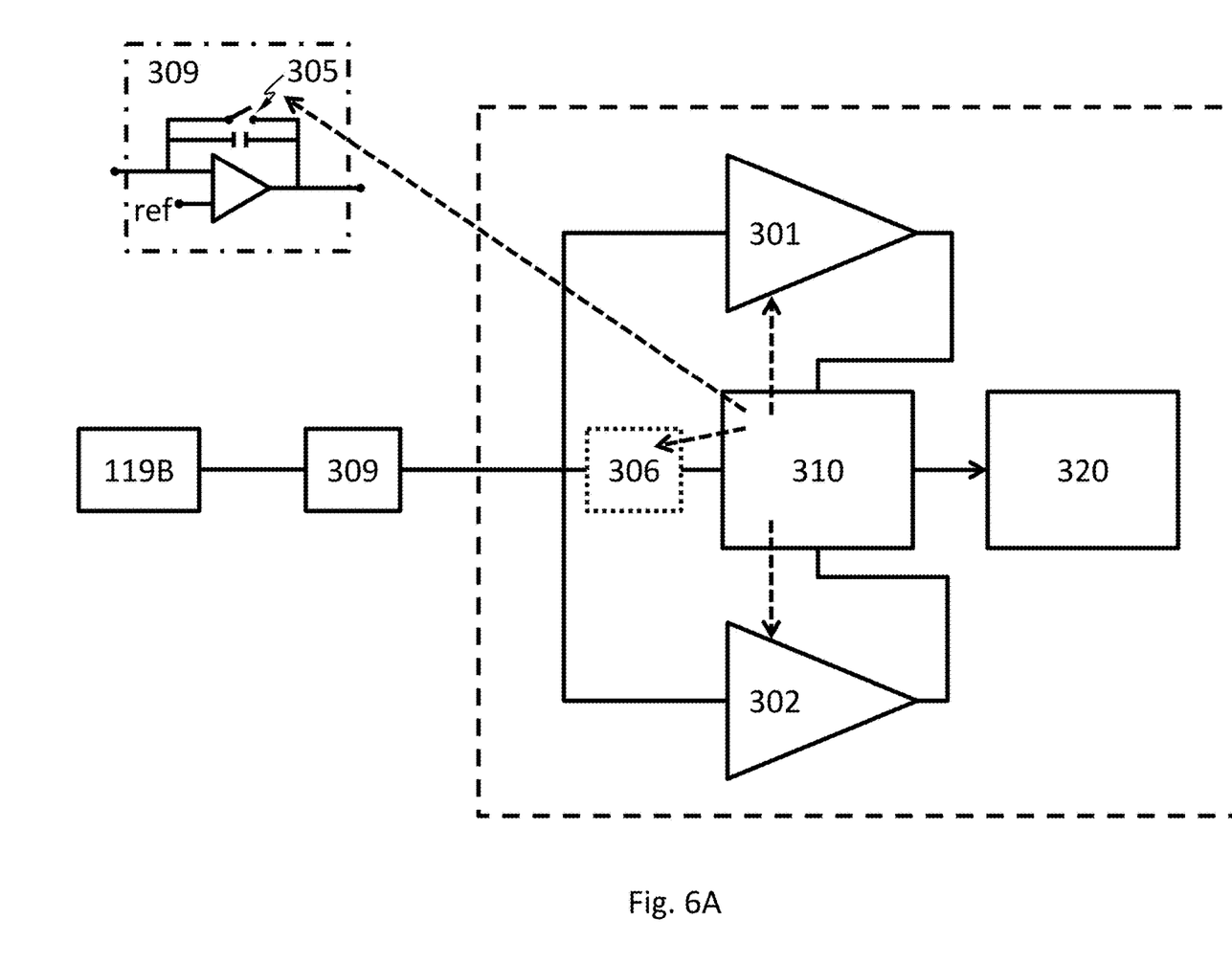
FIG. 6A and FIG. 6B each show a component diagram of an electronic system of the radiation detector in FIG. 5A, FIG. 5B and FIG. 5C, according to an embodiment.
Figure 6B:
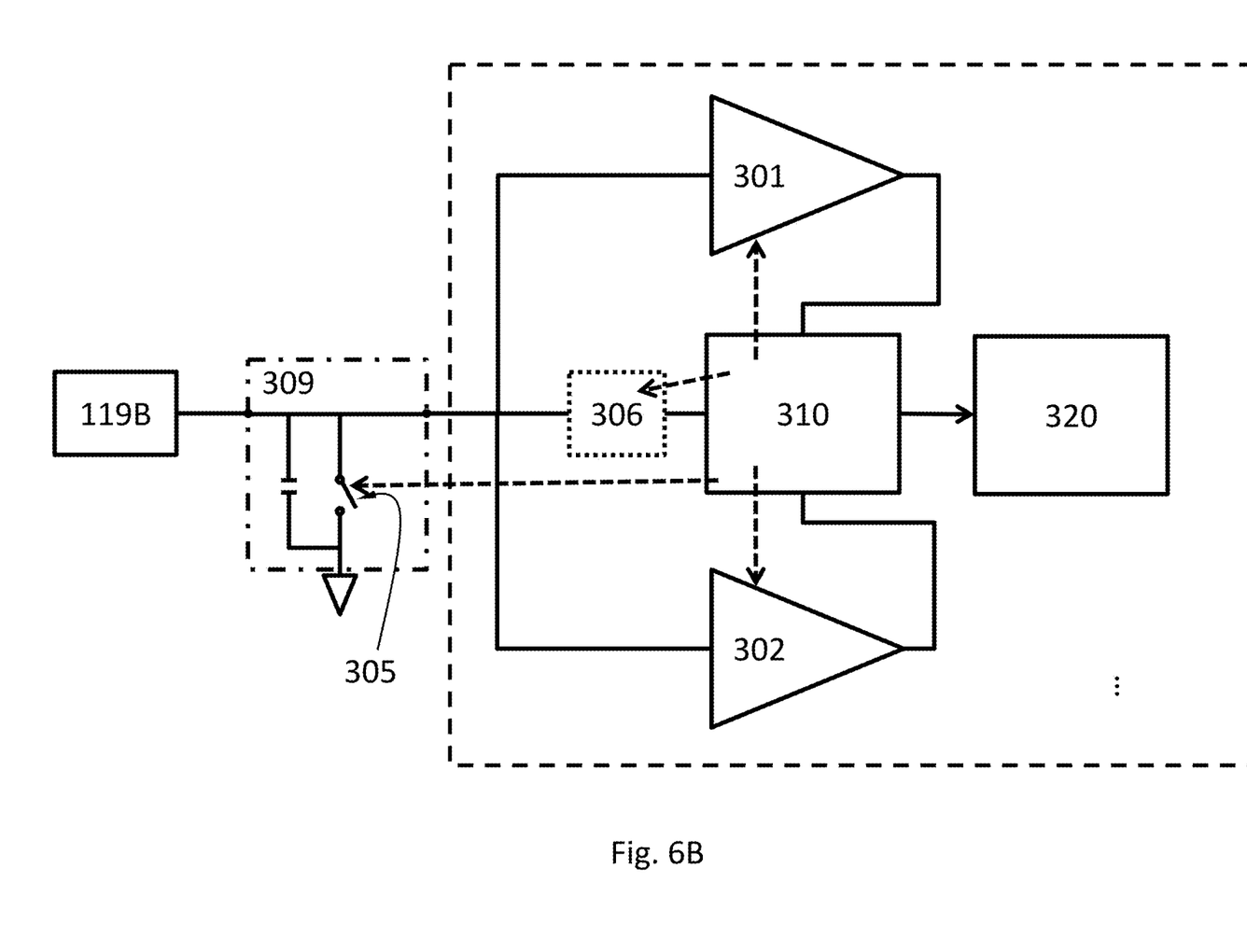

FIG. 6A and FIG. 6B each show a component diagram of the electronic system 121, according to an embodiment. The electronic system 121 may include a first voltage comparator 301, a second voltage comparator 302, a counter 320, a switch 305, an optional voltmeter 306 and a controller 310.

The first voltage comparator 301 is configured to compare the voltage of at least one of the electric contacts 119B to a first threshold. The first voltage comparator 301 may be configured to monitor the voltage directly, or calculate the voltage by integrating an electric current flowing through the electrical contact 119B over a period of time. The first voltage comparator 301 may be controllably activated or deactivated by the controller 310. The first voltage comparator 301 may be a continuous comparator. Namely, the first voltage comparator 301 may be configured to be activated continuously and monitor the voltage continuously. The first voltage comparator 301 may be a clocked comparator. The first threshold may be 5-10%, 10%-20%, 20-30%, 30-40% or 40-50% of the maximum voltage one incident particle of radiation may generate on the electric contact 119B. The maximum voltage may depend on the energy of the incident particle of radiation, the material of the radiation absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be configured to monitor the voltage directly or calculate the voltage by integrating an electric current flowing through the diode or the electrical contact over a period of time. The second voltage comparator 302 may be a continuous comparator. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, \text{ if } x \geq 0 \\ -x, \text{ if } x \leq 0 \end{cases}.$$

The second threshold may be 200%-300% of the first threshold. The second threshold may be at least 50% of the maximum voltage one incident particle of radiation may generate on the electric contact 119B. For example, the second threshold may be 100 mV, 150 mV, 200 mV, 250 mV or 300 mV. The second voltage comparator 302 and the first voltage comparator 301 may be the same component. Namely, the system 121 may have one voltage comparator that can compare a voltage with two different thresholds at different times.

The first voltage comparator 301 or the second voltage comparator 302 may comprise one or more op-amps or any other suitable circuitry. The first voltage comparator 301 or the second voltage comparator 302 may have a high speed to allow the electronic system 121 to operate under a high flux of incident particles of radiation. However, having a high speed is often at the cost of power consumption.

The counter 320 is configured to register a number of particles of radiation incident on the radiation absorption layer 110 comprising pixels 150. The counter 320 may be a software component (e.g., a number stored in a computer memory) or a hardware component (e.g., a 4017 IC and a 7490 IC).

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electrical contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero"

means that temporal change of the voltage is less than 0.1%/ns. The phase "the rate of change of the voltage is substantially non-zero" means that temporal change of the voltage is at least 0.1%/ns.

The controller 310 may be configured to activate the second voltage comparator during (including the beginning and the expiration) the time delay. In one embodiment, the controller 310 is configured to activate the second voltage comparator at the beginning or expiration of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause at least one of the number registered by the counter 320 to increase by one, if, during the time delay, the second voltage comparator 302 determines that the absolute value of the voltage equals or exceeds the absolute value of the second threshold.

The controller 310 may be configured to cause the optional voltmeter 306 to measure the voltage upon expiration of the time delay. The controller 310 may be configured to connect the electric contact 119B to an electrical ground, so as to reset the voltage and discharge any charge carriers accumulated on the electric contact 119B. In one embodiment, the electric contact 119B is connected to an electrical ground after the expiration of the time delay. In an embodiment, the electric contact 119B is connected to an electrical ground for a finite reset time period. The controller 310 may connect the electric contact 119B to the electrical ground by controlling the switch 305. The switch may be a transistor such as a field-effect transistor (FET).

In one embodiment, the system 121 has no analog filter network (e.g., a RC network). In an embodiment, the system 121 has no analog circuitry.

The voltmeter 306 may feed the voltage it measures to the controller 310 as an analog or digital signal.

The electronic system 121 may include an integrator 309 electrically connected to the electric contact 119B, wherein the integrator is configured to collect charge carriers from the electric contact 119B. The integrator 309 can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electric contact 119B accumulate on the capacitor over a period of time ("integration period"). After the integration period has expired, the capacitor voltage is sampled and then reset by a reset switch. The integrator 309 may include a capacitor directly connected to the electric contact 119B.

Figure 7:
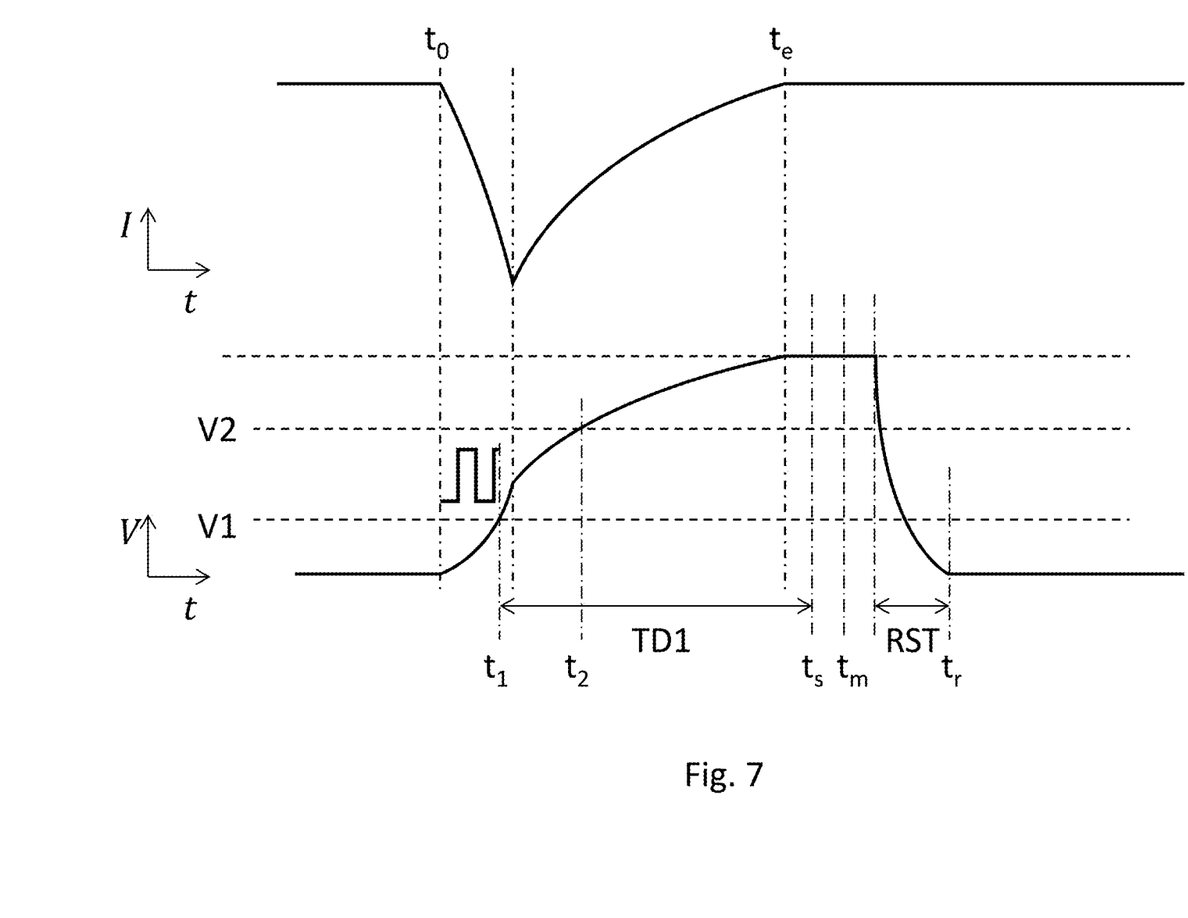
FIG. 7 schematically shows a temporal change of the electric current flowing through an electrode (upper curve) of a diode or an electric contact of a resistor of a radiation absorption layer exposed to radiation, the electric current caused by charge carriers generated by a particle of radiation incident on the radiation absorption layer, and a corresponding temporal change of the voltage of the electrode (lower curve), according to an embodiment.

FIG. 7 schematically shows a temporal change of the electric current flowing through the electric contact 119B (upper curve) caused by charge carriers generated by a particle of radiation incident on the pixel 150 encompassing the electric contact 119B, and a corresponding temporal change of the voltage of the electric contact 119B (lower curve). The voltage may be an integral of the electric current with respect to time. At time t0, the particle of radiation hits pixel 150, charge carriers start being generated in the pixel 150, electric current starts to flow through the electric contact 119B, and the absolute value of the voltage of the electric contact 119B starts to increase. At time $t_1$, the first voltage comparator 301 determines that the absolute value of the voltage equals or exceeds the absolute value of the first threshold V1, and the controller 310 starts the time delay TD1 and the controller 310 may deactivate the first voltage comparator 301 at the beginning of TD1. If the controller 310 is deactivated before $t_1$, the controller 310 is activated at $t_1$. During TD1, the controller 310 activates the second voltage comparator 302. The term "during" a time delay as used here means the beginning and the expiration (i.e., the end) and any time in between. For example, the controller 310 may activate the second voltage comparator 302 at the expiration of TD1. If during TD1, the second voltage comparator 302 determines that the absolute value of the voltage equals or exceeds the absolute value of the second threshold V2 at time $t_2$, the controller 310 waits for stabilization of the voltage to stabilize. The voltage stabilizes at time $t_e$, when all charge carriers generated by the particle of radiation drift out of the radiation absorption layer 110. At time $t_s$, the time delay TD1 expires. At or after time $t_e$, the controller 310 causes the voltmeter 306 to digitize the voltage and determines which bin the energy of the particle of radiation falls in. The controller 310 then causes the number registered by the counter 320 corresponding to the bin to increase by one. In the example of FIG. 7, time $t_s$ is after time $t_e$; namely TD1 expires after all charge carriers generated by the particle of radiation drift out of the radiation absorption layer 110. If time $t_e$ cannot be easily measured, TD1 can be empirically chosen to allow sufficient time to collect essentially all charge carriers generated by a particle of radiation but not too long to risk have another incident particle of radiation. Namely, TD1 can be empirically chosen so that time $t_s$ is empirically after time $t_e$. Time $t_s$ is not necessarily after time $t_e$ because the controller 310 may disregard TD1 once V2 is reached and wait for time $t_e$. The rate of change of the difference between the voltage and the contribution to the voltage by the dark current is thus substantially zero at $t_e$. The controller 310 may be configured to deactivate the second voltage comparator 302 at expiration of TD1 or at $t_2$, or any time in between.

The voltage at time $t_e$ is proportional to the amount of charge carriers generated by the particle of radiation, which relates to the energy of the particle of radiation. The controller 310 may be configured to determine the energy of the particle of radiation, using the voltmeter 306.

After TD1 expires or digitization by the voltmeter 306, whichever later, the controller 310 connects the electric contact 119B to an electric ground for a reset period RST to allow charge carriers accumulated on the electric contact 119B to flow to the ground and reset the voltage. After RST, the electronic system 121 is ready to detect another incident particle of radiation. If the first voltage comparator 301 has been deactivated, the controller 310 can activate it at any time before RST expires. If the controller 310 has been deactivated, it may be activated before RST expires.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method comprising:
moving an image sensor along a first direction among a plurality of positions relative to a scene and capturing partial images of the scene respectively at the plurality of positions; and
forming an image of the scene from the partial images;
wherein the image sensor has an active area and a dead zone;
wherein the dead zone extends along a second direction;
wherein the second direction is at an angle with the first direction; and
wherein each point in the scene falls on the dead zone no more than once when the image sensor is at the plurality of positions.

2. The method of claim 1, wherein the dead zone extends across the active area.

3. The method of claim 1, wherein the dead zone divides the active area into multiple spatially discontinuous portions.

4. The method of claim 1, wherein the image sensor comprises a plurality of radiation detectors.

5. The method of claim 4, wherein the plurality of radiation detectors overlap one another.

6. The method of claim 4, wherein at least one of the plurality of radiation detectors has an edge parallel to the first direction.

7. The method of claim 4, wherein at least one of the plurality of radiation detectors comprises:
a radiation absorption layer comprising an electric contact;
a first voltage comparator configured to compare a voltage of the electric contact to a first threshold;
a second voltage comparator configured to compare the voltage to a second threshold;
a counter configured to register a number of particles of radiation incident on the radiation absorption layer;
a controller;
wherein the controller is configured to start a time delay from a time at which the first voltage comparator determines that an absolute value of the voltage equals or exceeds an absolute value of the first threshold;
wherein the controller is configured to activate the second voltage comparator during the time delay; and
wherein the controller is configured to cause at least one of the numbers of particles of radiation to increase by one, when the second voltage comparator determines that an absolute value of the voltage equals or exceeds an absolute value of the second threshold.

8. The method of claim 7, wherein the image sensor further comprises an integrator electrically connected to the electric contact, wherein the integrator is configured to collect charge carriers from the electric contact.

9. The method of claim 7, wherein the controller is configured to activate the second voltage comparator at a beginning or an expiration of the time delay.

10. The method of claim 7, wherein the controller is configured to connect the electric contact to an electrical ground.

11. The method of claim 7, wherein a rate of change of the voltage is substantially zero at an expiration of the time delay.

12. The method of claim 7, wherein the radiation absorption layer comprises single-crystalline silicon.

13. The method of claim 7, wherein the image sensor does not comprise a scintillator.

14. The method of claim 4, wherein the plurality of radiation detectors is arranged on a planar surface of a support, and wherein radiation-receiving surfaces of the plurality of radiation detectors are tilted relative to the planar surface of the support.

15. The method of claim 4, wherein the plurality of radiation detectors comprises a first radiation detector and a second radiation detector, wherein the first radiation detector is arranged in a different orientation than the second radiation detector.

16. The method of claim 4, wherein the plurality of radiation detectors comprises a first radiation detector and a second radiation detector, wherein the first radiation detector has an edge parallel to the first direction and the second radiation detector has an edge parallel to the second direction.

17. The method of claim 1, further comprising forming projections of guard rings in the partial images.

18. The method of claim 1, wherein the image sensor comprises a plurality of pixels; wherein the image sensor is configured to count numbers of particles of radiation incident on the plurality of pixels, within a period of time.

19. The method of claim 18, wherein the particles of radiation are X-ray photons.

* * * * *